(12) United States Patent
Minemura et al.

(10) Patent No.: US 8,997,615 B2
(45) Date of Patent: Apr. 7, 2015

(54) MICROTOME AND CRYOSTAT

(75) Inventors: Hiroyuki Minemura, Nagano (JP);
Tatsuya Seki, Nagano (JP)

(73) Assignees: Sakura Seiki Co., Ltd., Nagano (JP);
Sakura Finetek Japan Co., Ltd., Tokyo (JP)

( * ) Notice: Subject to any disclaimer, the term of this patent is extended or adjusted under 35 U.S.C. 154(b) by 248 days.

(21) Appl. No.: 13/816,458

(22) PCT Filed: Jul. 29, 2011

(86) PCT No.: PCT/JP2011/067390
§ 371 (c)(1),
(2), (4) Date: Feb. 11, 2013

(87) PCT Pub. No.: WO2012/023405
PCT Pub. Date: Feb. 23, 2012

(65) Prior Publication Data
US 2013/0137163 A1    May 30, 2013

(30) Foreign Application Priority Data

Aug. 18, 2010    (JP) ................................ 2010-182767

(51) Int. Cl.
*B26D 7/10*    (2006.01)
*A01N 1/02*    (2006.01)
*G01N 1/06*    (2006.01)

(52) U.S. Cl.
CPC ............... *A01N 1/0257* (2013.01); *G01N 1/06* (2013.01); *Y10S 83/9155* (2013.01)

(58) Field of Classification Search
CPC ........................................................ G01N 1/06
USPC ........ 83/170, 171, 915.5, 699.51, 452; 279/5; 82/162, 170; 403/123, 114; 269/71; 215/312

See application file for complete search history.

(56) References Cited

U.S. PATENT DOCUMENTS 5,711,200 A * 1/1998 Thiem .............................. 83/170
5,782,572 A * 7/1998 Thiem .............................. 403/90
(Continued)

FOREIGN PATENT DOCUMENTS

| JP | U6335941 | 3/1988 |
| JP | 09043114 | 2/1997 |
| JP | 09318502 | 2/1997 |
| JP | 10111219 | 4/1998 |

(Continued)

*Primary Examiner* — Boyer D Ashley
*Assistant Examiner* — Richard Crosby, Jr.
(74) *Attorney, Agent, or Firm* — Blakely Sokoloff Taylor & Zafman LLP

(57) ABSTRACT

A microtome comprising a head 32 which holds a sample, an alignment mechanism 50 which aligns the head 32, a body portion 42 which is provided on a back face side of the alignment mechanism 50, a cylindrical coupling portion 41 which couples the body portion 42 with the head 32, a temperature controller 34 in the head 32, and refrigerant piping 40 and electrical wiring 46 for the temperature controller 34, and the alignment mechanism 50 includes a spherical member 68 coupled with the back face side of the head and having a spherical outer periphery and includes retainer portions 70 and 71 retaining the outer periphery of the spherical member 68 slidably along a spherical surface, the spherical member 68 has a through hole 74 which communicates with the hollow portion 43 of the coupling portion 41, the refrigerant piping 40 and the electrical wiring 46 are connected with the temperature controller 34 in the head 32 through the through hole 74 of the spherical member 68 and the hollow portion 43 of the coupling portion 41.

14 Claims, 9 Drawing Sheets

(56) References Cited

U.S. PATENT DOCUMENTS

| | | | |
|---|---|---|---|
| 5,960,640 A * | 10/1999 | Teppke | 62/320 |
| 7,673,546 B2 * | 3/2010 | Dorenkamp et al. | 83/170 |
| 8,608,398 B2 * | 12/2013 | Mekid | 403/90 |
| 2007/0204734 A1 * | 9/2007 | Ito et al. | 83/170 |
| 2009/0183613 A1 * | 7/2009 | Lihl et al. | 83/167 |

FOREIGN PATENT DOCUMENTS

| | | |
|---|---|---|
| JP | 3732297 | 10/2005 |
| JP | 2006510000 | 3/2006 |
| JP | 3950207 | 4/2007 |
| JP | 2007192606 | 8/2007 |
| JP | 4142647 | 6/2008 |

* cited by examiner

MICROTOME AND CRYOSTAT

CROSS-REFERENCE TO RELATED APPLICATION

This application is the National Stage of International Patent Application No. PCT/JP2011/067390, filed Jul. 29, 2011.

TECHNICAL FIELD

The present invention relates to a microtome and a cryostat including a microtome for preparing a tissue specimen by slicing a tissue in a low-temperature condition.

BACKGROUND ART

For example, in an operation for carcinoma excision, it is required to confirm tissues of an organ developing a cancer and to study how deep the organ should be excised. In such a case, a tissue specimen prepared by slicing a part of the organ is observed.

By the way, although tissue specimens are ordinarily treated with paraffin substitution, there is not enough time to conduct paraffin substitution when a tissue specimen is rapidly prepared during operation or the like.

Thus cryostats for rapidly preparing tissue specimens while organs are frozen have been conventionally known.

The cryostat includes a chamber for freezing a pathological tissue (hereinafter, it may be simply called a sample), and in the chamber, a microtome for slicing the sample while the frozen state is held is provided (For example, Patent Literature 1).

The microtome includes a head holding the sample, a cooling device for maintaining the sample held by the head at a lower temperature than in the chamber, and a blade for slicing the sample held by the head (For example, Patent Literature 2).

In addition, the microtome has an alignment mechanism which aligns the head to align the sample relative to the blade for slicing (For example, Patent Literature 3).

CITATION LIST

Patent Literature

PTL 1: Japanese Patent Publication No. 3950207
PTL 2: Japanese Patent Publication No. 4142647
PTL 3: Japanese Patent Publication No. 3732297

SUMMARY OF INVENTION

Technical Problem

Sections of the sliced sample or the like may be scattered in the microtome. Since the sample contains a substance suspected to cause infections, the circumference of the head should be cleaned in every part for preventing infections.

Meanwhile, the heads of the microtomes disclosed in each of the above-mentioned patent literatures are equipped with refrigerant piping for refrigerant circulation, a Peltier element, and electrical wiring of a thermosensor, for regulating a temperature by cooling and heating to a temperature suitable for slicing the sample. The refrigerant piping and the electrical wiring are generally connected to a lower part and a lateral side of the head.

For this reason, the refrigerant piping and the electrical wiring are impeditive in the conventional microtomes and cryostats therewith, and complete cleaning is therefore inhibited.

In addition, in the case that the refrigerant piping and the electrical wiring are provided around the head, there are problems that they are also impeditive in works in applying the sample to the head and adjusting an alignment of the head relative to the blade.

Thus the present invention has been made to solve the above problems, and an object thereof is to provide a microtome and a cryostat including this microtome which are produced so that cleaning and other works can be surely conducted while the refrigerant piping and the electrical wiring are not impeditive.

Solution to Problem

Characteristically, the microtome related to the present invention includes a cutting blade attached to a blade holder, a head which holds the sample so that a surface side of the sample faces the cutting blade, an alignment mechanism which is provided on the back side of the head and aligns the head so that the head can rotate in a vertical direction and in a horizontal direction perpendicular to the vertical direction, a body portion which is provided on the back side of the alignment mechanism and has an contact separation mechanism allowing the head to contact with and separate from the cutting blade, a cylindrical coupling portion which has a hollow portion in the center and connects the body portion with the head, a temperature controller provided in the head for cooling or heating the sample held by the head, refrigerant piping for circulating a refrigerant in the temperature controller, and electrical wiring for the temperature controller, wherein the alignment mechanism includes a spherical member connected with the back side of the head and having a spherical outer periphery and includes a retainer portion holding the outer periphery of the spherical, member slidably along a spherical surface, the spherical member has a through hole communicating with the hollow portion of the coupling portion, and the refrigerant piping and the electrical wiring are connected with the temperature controller in the head through the through hole of the spherical member and the hollow portion of the coupling portion.

Use of this constitution allows the refrigerant piping and the electrical wiring to be connected with the inner part of the head from the back side, and they are prevented from being exposed to an under surface and a lateral side of the head. Thereby, even when sections of the sample are scattered around the head, the refrigerant piping and the electrical wiring are not impeditive, resulting in sure cleaning around the head. In addition, even when works other than cleaning are conducted, the refrigerant piping and the electrical wiring are not impeditive.

In addition, characteristically, the inner wall surface on the back side of the spherical member is spherically formed, and its outer periphery is spherically formed so as to slidably contact with the inner wall surface of the spherical member, on which a ring-shaped member in which a second through hole communicating between the above-mentioned through hole and hollow portion is formed in the center is provided, vertically moving means which vertically rotates the head by vertically moving the ring-shaped member is provided, and horizontally moving means which horizontally rotates the head by horizontally moving the ring-shaped member is provided.

According to this constitution, the refrigerant piping and the electrical wiring are not impeditive, and a direction of the sample relative to the cutting blade can be adjusted with a high degree of accuracy.

Furthermore, characteristically, the vertically moving means may have a linear portion which is horizontally and linearly formed on an upper edge or lower edge of the ring-shaped member and a vertically pressing shaft which can freely move horizontally relative to the linear portion and is formed to be capable of vertically pressing the linear portion, and the horizontally moving means may have a linear portion which is vertically and linearly formed on a left side or right side of the ring-shaped member, and a horizontally pressing shaft which can freely move vertically relative to the linear portion and is formed to be capable of horizontally pressing the linear portion.

According to this constitution, when the head is vertically or horizontally aligned, the alignment can be surely conducted with a high degree of accuracy without interfering each rotation in the vertical and horizontal direction.

Furthermore, the refrigerant piping located in the through hole may characteristically include a member which can be bent in any direction.

According to this constitution, when the head is aligned, the refrigerant piping can flexibly follow the alignment. This can avoid a stress to the refrigerant piping to prevent breakage or the like of the refrigerant piping.

In addition, characteristically, the coupling portion may include an introduction hole for introducing the refrigerant piping and the electrical wiring into the hollow portion of the coupling portion, and the refrigerant piping and the electrical wiring positioned from the introduction hole to the outside of the coupling portion are provided by being bent so as to follow the movement of the coupling portion by the contact separation mechanism.

According to this constitution, the refrigerant piping and the electrical wiring can sufficiently follow the movement of the coupling portion.

The cutting blade may be characterized by the points that the blade holder has an attachment space into which the cutting blade enters for attachment and is equipped with magnets for attracting the cutting blade entering the attachment space.

According to the constitution, when the cutting blade is replaced, the cutting blade can be easily detached, and falling of the cutting blade can be prevented, and thereby the cutting blade can be stably replaced.

The cryostat related to the present invention is characterized by including a chamber having a cooling function and the microtome described in any one of claims 1-6.

Use of this constitution surely permits cleaning in the chamber and other works while the refrigerant piping and the electrical wiring are not impeditive.

Characteristically, only the blade holder to which the cutting blade is attached and the head of the microtome may be located in the chamber.

In other words, when the whole of the microtome is provided in the chamber, the volume of the chamber should be increased, resulting in enlarging the capacity of the cooling function. For this reason, requests such as downsizing and electric power saving of the device could not have been responded, but downsizing and electric power saving of the device can be achieved by using this constitution.

Characteristically, a portion from which the head of the microtome projects may be covered with a deformable and fluid-tight material in an inner wall surface of the chamber.

Thereby, even if the head is moved by the motion of the body portion of the microtome outside of the chamber, interference with the inner wall surface of the chamber can be avoided.

Advantageous Effects of Invention

The microtome and the cryostat of the present invention surely permit cleaning and other works because the refrigerant piping and the electrical wiring are not impeditive.

DESCRIPTION OF EMBODIMENTS

Figure 1:
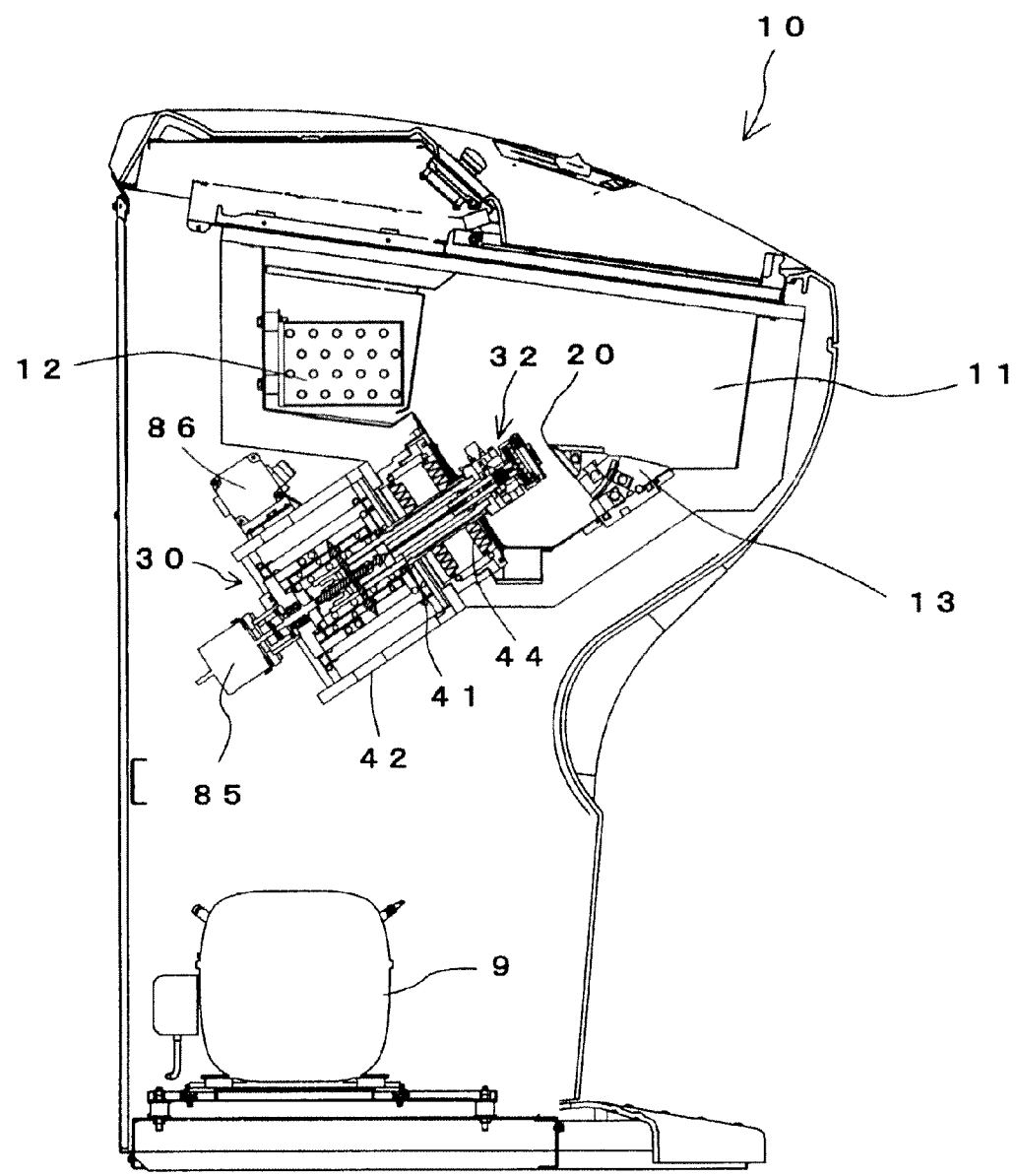
FIG. 1 illustrates a side cross-sectional view of the internal constitution of the cryostat related to the present invention.
Figure 2:
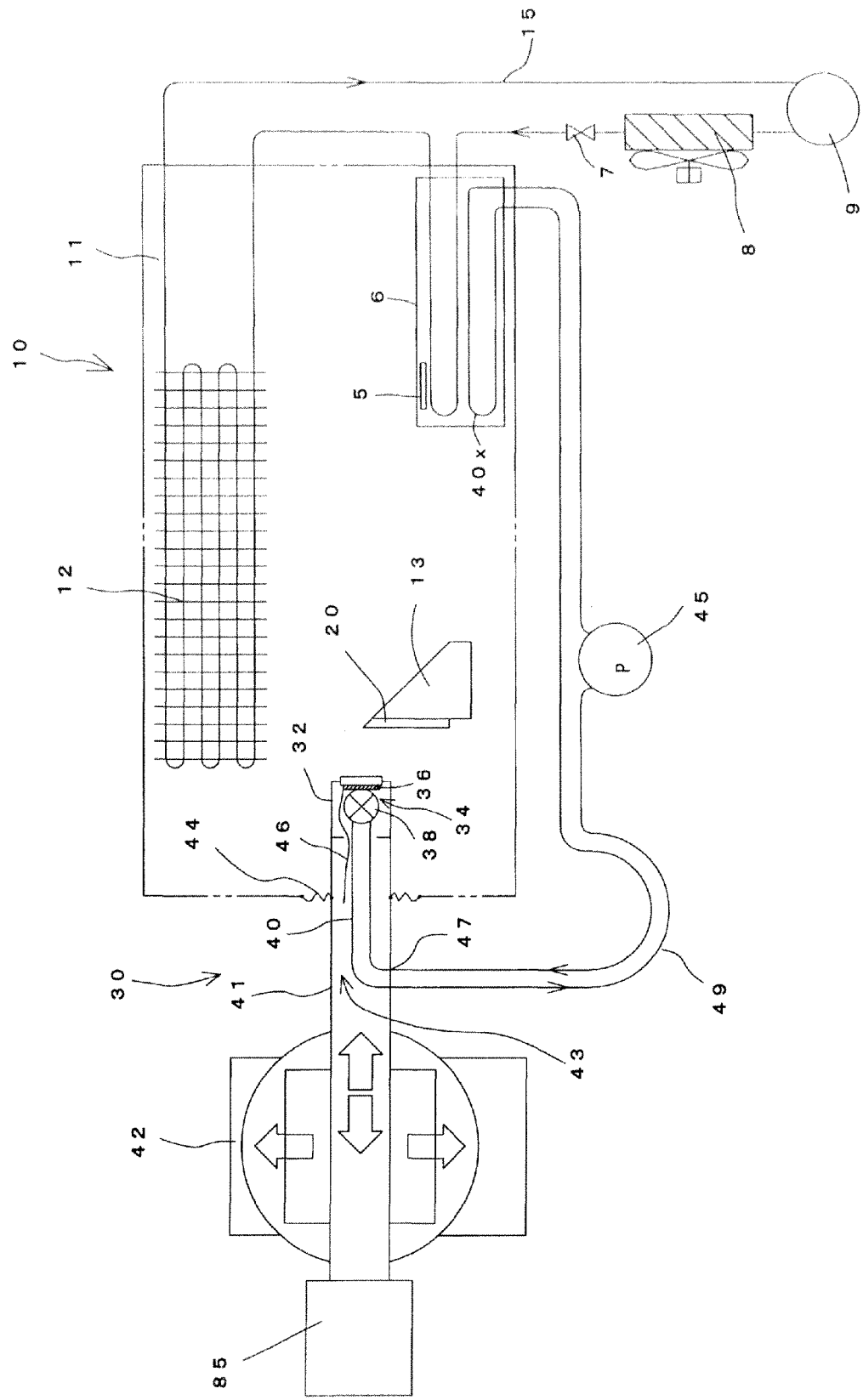
FIG. 2 illustrates a schematic view of the internal constitution of the cryostat.

The side view of the whole constitution of the cryostat in the present embodiment is illustrated in FIG. 1, and the explanatory schematic view of the cryostat in the present embodiment is illustrated in FIG. 2.

First, the whole constitutions of a cryostat 10 and a microtome 30 will be explained on the basis of these figures.

The cryostat 10 is a device to rapidly prepare a tissue specimen by freezing a sample and is often used mainly in surgery.

The cryostat 10 includes a chamber 11 in which works are conducted for preparing the tissue specimen, a cooling device (the cooling function in Claims) 12 which cools the inside of the chamber 11, and the microtome 30.

The cooling device 12, a blade holder 13 having a cutting blade 20 of the microtome 30, and a head 32 of the microtome 30 are provided in the chamber 11 of the cryostat 10. The head 32 is located opposed to the cutting blade 20 and holds the sample.

The cooling device 12 which cools the inside of the chamber 11 is an evaporator for a refrigerant. A compressor 9 which compresses the refrigerant, a condenser 8 which releases heat to the outside and an expansion valve 7 are connected with the cooling device 12 through the chamber refrigerant piping 15, and heat exchange is performed by circulating the refrigerant among these devices to cool the inside of the chamber 11. The compressor 9, the condenser 8 and the expansion valve 7 are provided outside of the chamber 11.

A sample-preparing part 6 is provided in the chamber 11. The sample-preparing part 6 is a portion for preparation by freezing a block of the tissue sample to be attached to a sample-supporting part 51 (see FIG. 4 and FIG. 5) of the head 32. The operator can prepare the sample on the sample-preparing part 6.

The chamber refrigerant piping 15 constituting the cooling device 12 is provided in the sample-preparing part 6, and the sample-preparing part 6 can be cooled by the refrigerant passing through the chamber refrigerant piping 15. In addition, a Peltier element 5 is provided in the vicinity of the chamber refrigerant piping 15 in the sample-preparing part 6. When the Peltier element 5 is activated, the temperature of the top surface of a part on which the Peltier element 5 is provided can be lowered than those of other positions in the sample-preparing part 6. For this reason, in a portion of the sample-preparing part 6 on which the Peltier element 5 is provided, a tissue specimen block can be prepared by freezing earlier than that on the other portions in the sample-preparing part 6.

The blade holder 13 with the cutting blade 20 is fixed in the chamber 11, and the head 32 of the microtome 30 moves relative to the cutting blade 20, and thereby the sample is sliced. It should be noted that the detailed constitution about the blade holder 13 will be mentioned later.

Additionally, the head 32 of the microtome 30 is provided in the chamber 11, and a body portion 42 of the microtome 30 is provided outside of the chamber 11. A cylindrical coupling portion 41 in which a hollow portion 43 is formed links the head 32 with the body portion 42.

On the inner wall surface of the chamber 11, the coupling portion 41 extending from the back side of the head 32 to the body portion 42 is provided on a portion where the head 32 projects into the chamber 11, but the coupling portion 41 may project into the chamber 11 and move in other directions by motion of the body portion 42. At this time, in case the coupling portion 41 and the inner wall surface of the chamber 11 interfere with each other, a rubber seal 44 is provided around the coupling portion 41 on the inner wall surface of the chamber 11.

The rubber seal 44 is formed in a concertina shape to facilitate motion of the coupling portion 41 and prevent leakage of cold air in the chamber 11 to the outside.

The body portion 42 is fixed to the external surface of the chamber 11, and a motor 85 as means for migration which moves the coupling portion 41 connected to the head 32 forward and backward is provided on the back side in order to make the head 32 to approach and leave from the cutting blade 20, The motor 85 rotates by an operation from an operating section not shown and can move the head 32 in micrometers forward and backward by conversion means such as a gear which converts rotary motion into linear motion.

The motor 86 as the means for migration which moves the coupling portion 41 connected to the head 32 forward and backward is provided on the top surface of the body portion 42. The motor 86 rotates by an operation from an operating section not shown and vertically moves the head 32 by conversion means such as a gear which converts rotary motion into linear motion. The sample attached to the head 32 can be sliced while the sample is moved to the cutting blade 20 in a direction of the cutting by these motors.

Structurally the vertical motion of the coupling portion 41 can be also made by using a rotating handle not shown, without using the motor 86.

A temperature controller 34 is provided in the head 32 which supports the sample at a position opposed to the cutting blade 20.

The temperature controller 34 has a Peltier element 36 attached to the back side of the head 32, a heatsink 38 which is attached to the back side of the Peltier element 36 and includes a circulation duct in which the refrigerant circulates, and refrigerant piping 40 which circulates the refrigerant for the heatsink 38.

The refrigerant piping 40 is formed in a circular pattern, and in its course, a pump 45 is provided to circulate the refrigerant by drive of the pump 45. In the heatsink 38, heat generated in the Peltier element 36 is absorbed by the refrigerant, and the heated refrigerant is sent to an end part opposite a side connected to the heatsink 38 of the refrigerant piping 40 through the refrigerant pump 45. The end part 40x opposite the side connected to the heatsink 38 of the refrigerant plumbing 40 is positioned on the sample-preparing part 6 in the chamber 11. In other words, the refrigerant heated by absorbing heat from the Peltier element 36 of the head 32 is to be cooled down by heat exchange with the refrigerant in the chamber refrigerant piping 15 in the sample-preparing part 6.

The alignment mechanism is provided on the back side of the head 32, and the alignment mechanism will be mentioned later.

The coupling portion 41 is provided on the further back side of the alignment mechanism, and the refrigerant piping 40 and electrical wiring 46 for controlling the Peltier element 36 are positioned in the hollow portion 43 in the coupling portion 41. Thus the refrigerant piping 40 and the electrical wiring 46 are not exposed to the inside of the chamber 11, but are extended from the back side of the head 32 to the outside of the chamber 11 through the coupling portion 41.

For this reason, there are not the refrigerant piping 40 and the electrical wiring 46 around the head 32 in the chamber 11, and the work efficiency of cleaning for removal of the scattered sections, other works or the like can be enhanced.

In addition, an introduction hole 47 for introducing the refrigerant piping 40 and the electrical wiring 46 into the hollow portion 43 is formed in a certain place in the outside of the chamber 1 of the coupling portion 41. The introduction hole 47 is provided between the body portion 42 and the chamber 11.

The refrigerant piping 40 and the electrical wiring 46 outside of the coupling portion 41 in the vicinity of the introduction hole 47 have a curve 49 provided by being bent so as to follow the movement of the coupling portion 41.

Subsequently, the appearances and internal constitutions of the head and the alignment mechanism are shown in FIG. 3 to FIG. 8.

Figure 3:
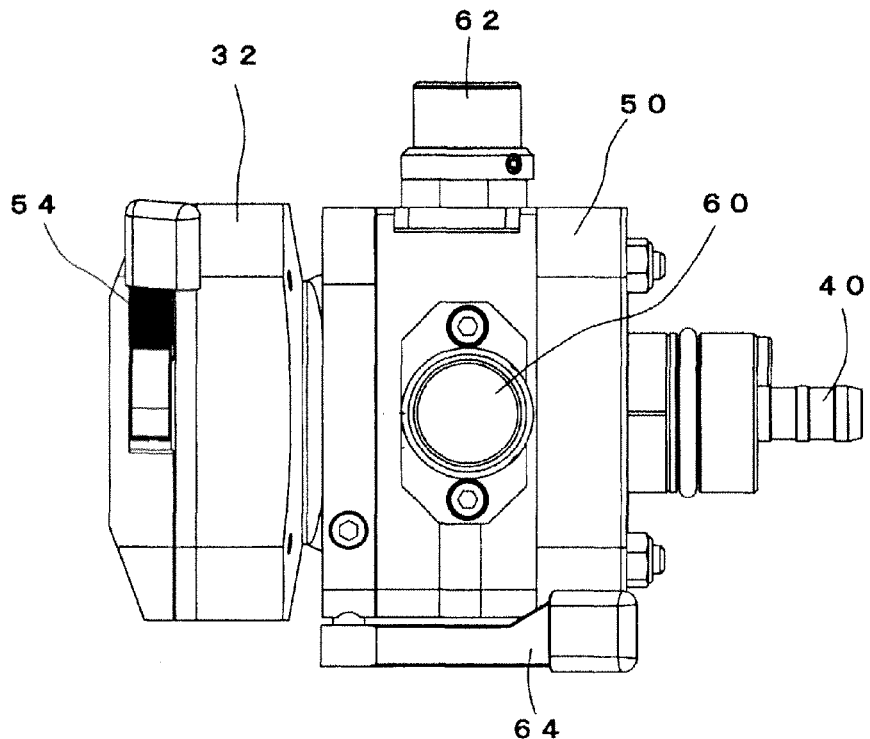
FIG. 3 illustrates a top view of the aspects of the head and the alignment mechanism.
Figure 4:
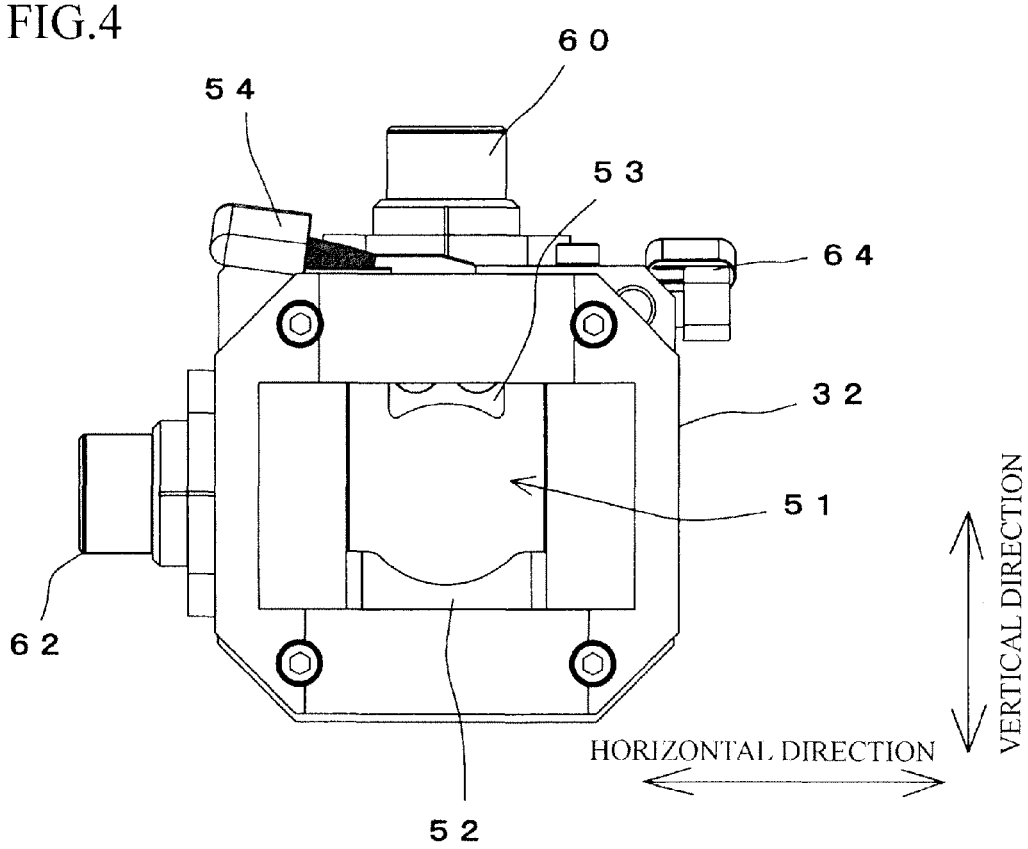
FIG. 4 illustrates a front view of the aspects of the head and the alignment mechanism.
Figure 5:
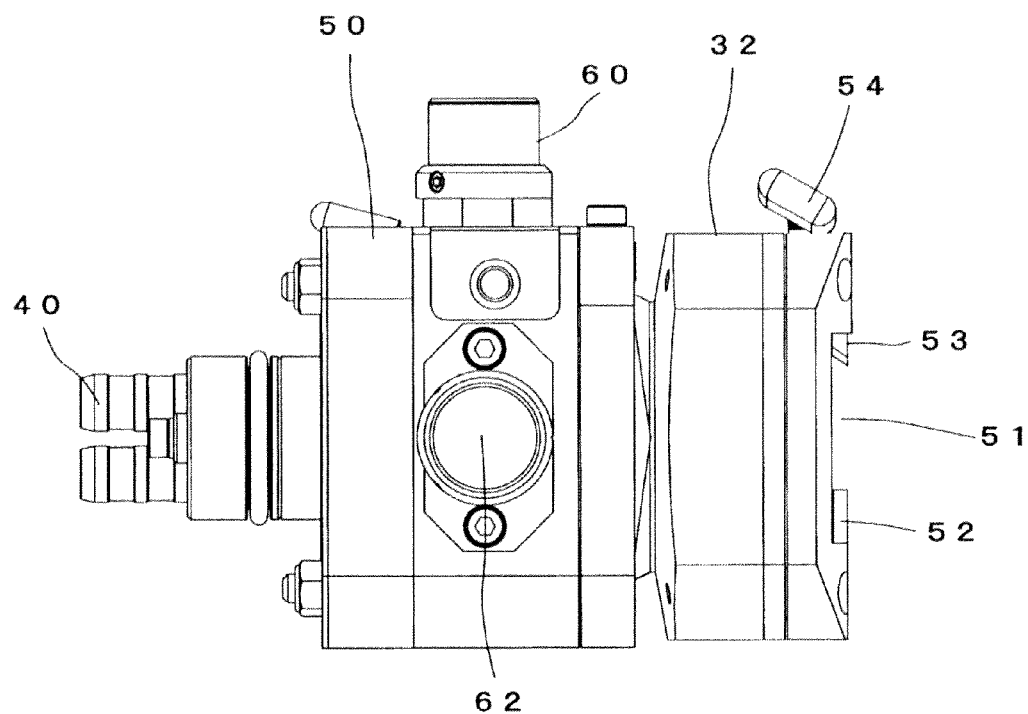
FIG. 5 illustrates a side view of the aspects of the head and the alignment mechanism.
Figure 6:
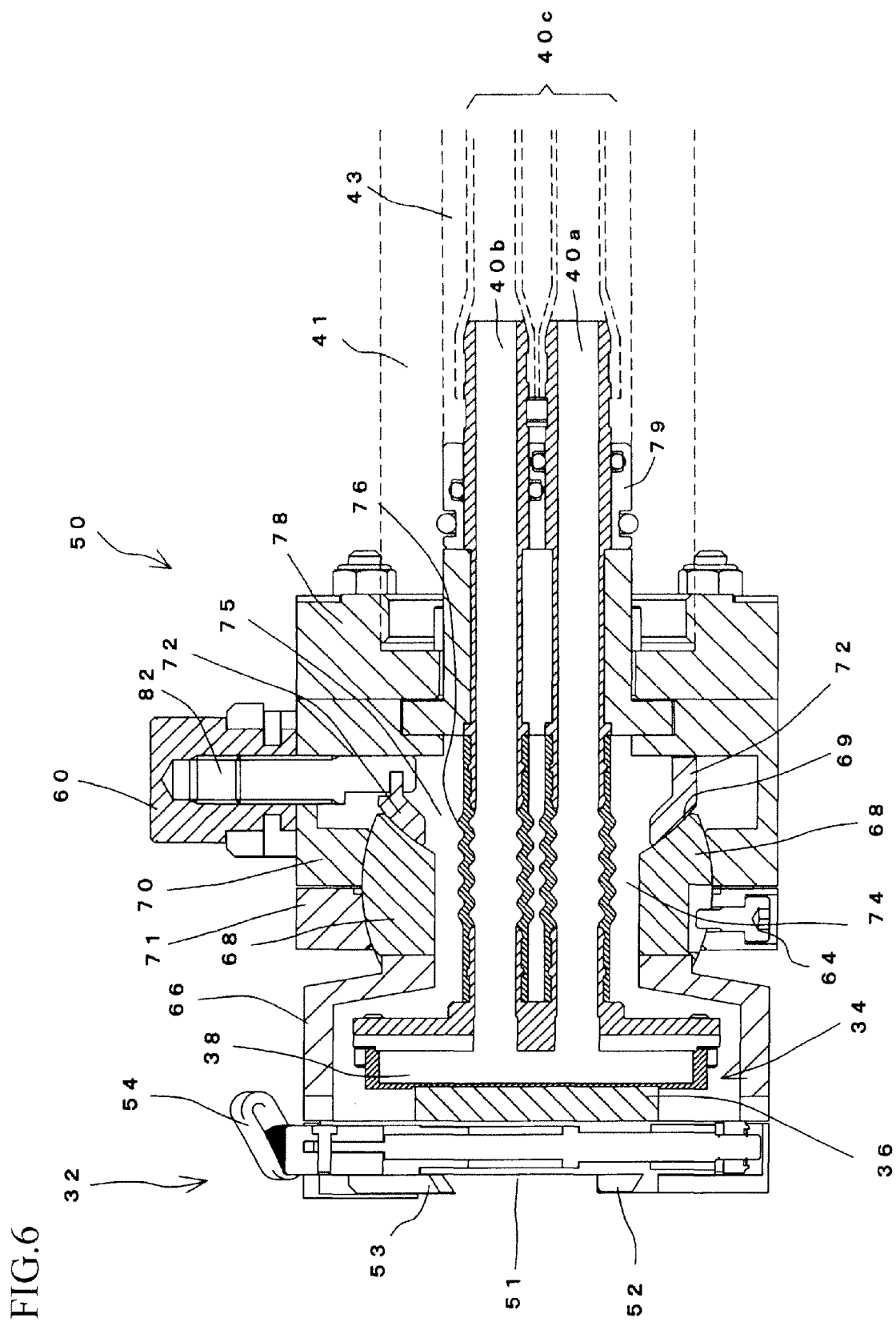
FIG. 6 illustrates a cross-sectional view of the internal constitutions of the head and the alignment mechanism.
Figure 7:
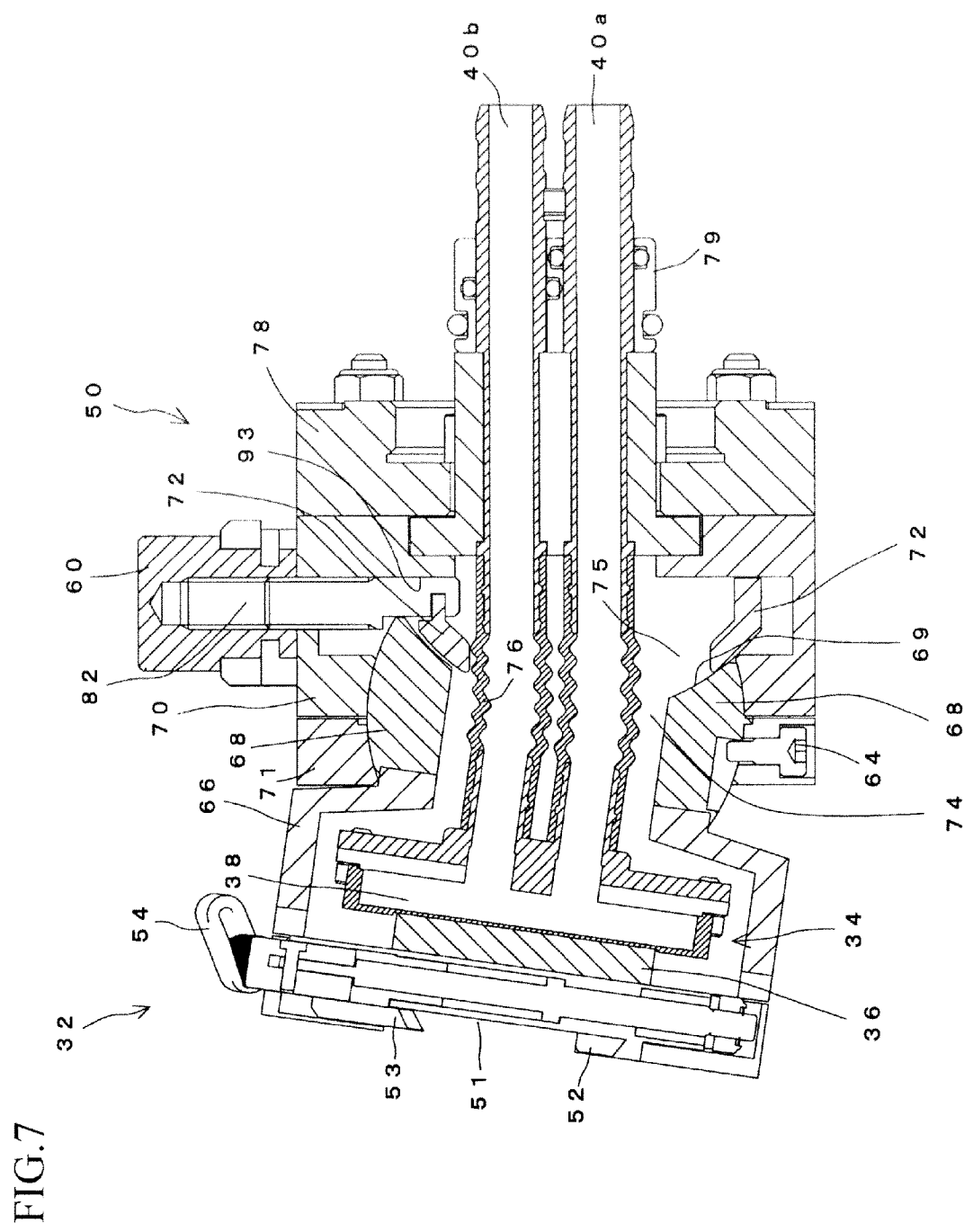
FIG. 7 illustrates a cross-sectional view of a state where the head is aligned upward in FIG. 6.
Figure 8:
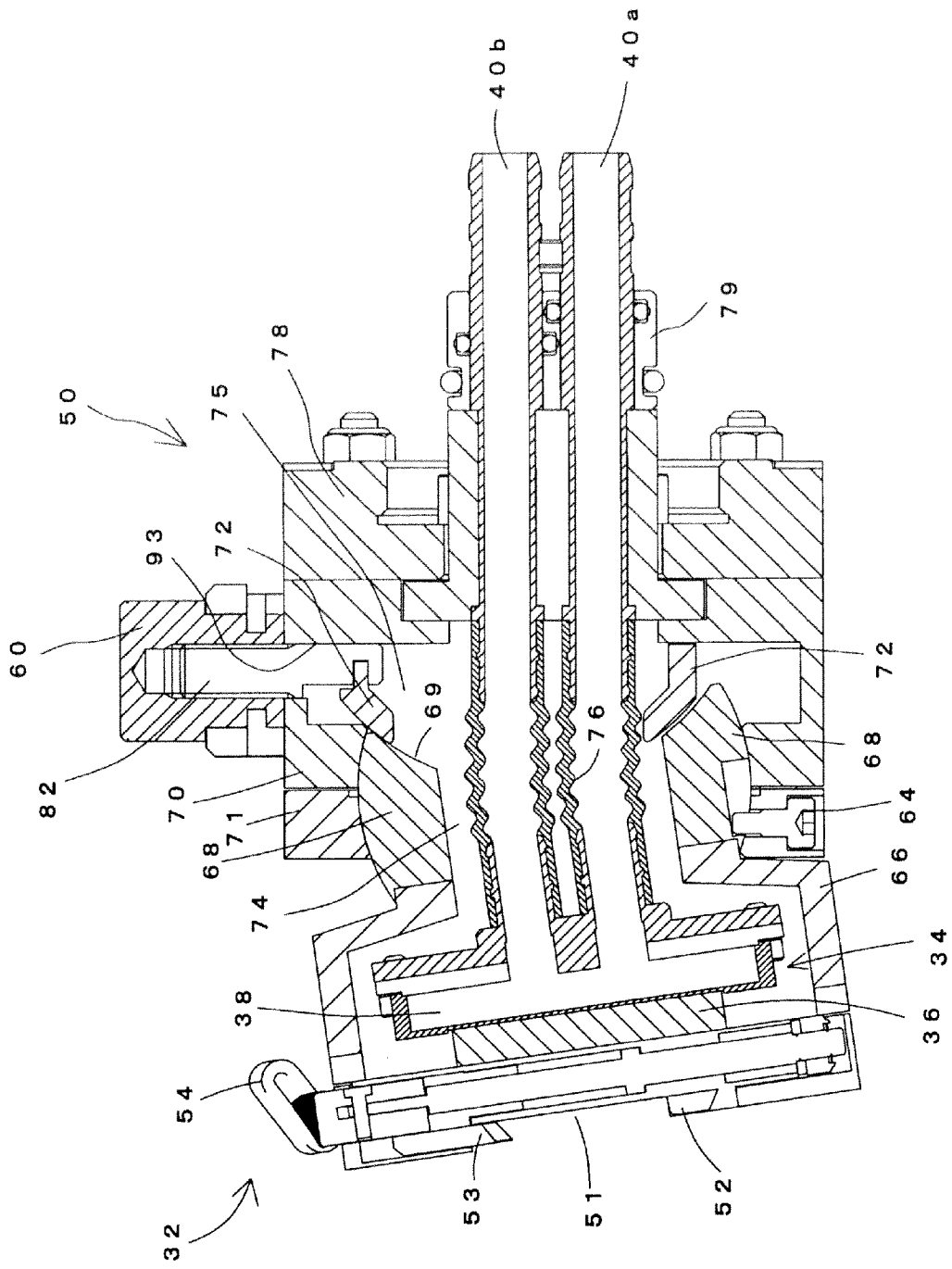
FIG. 8 illustrates a cross-sectional view of a state where the head is aligned downward in FIG. 6.
Figure 9:
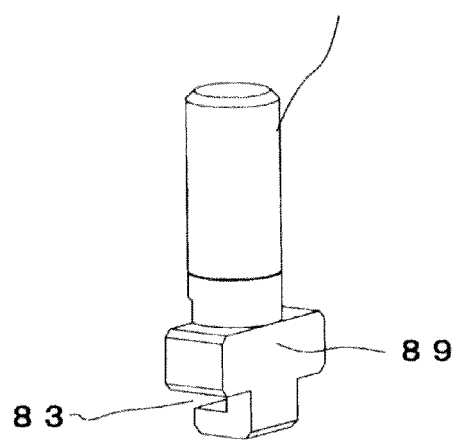
FIG. 9 illustrates an explanatory drawing of the appearances of the vertical moving member and the horizontal moving member.
Figure 10A:
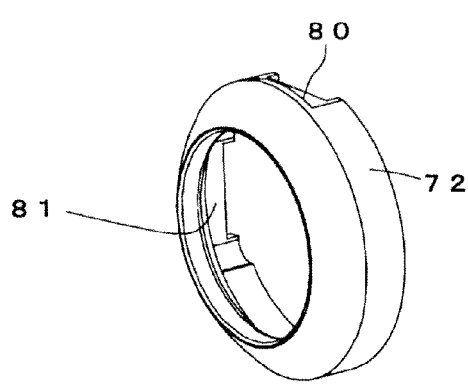
FIG. 10A and FIG. 10B illustrate explanatory drawings of the appearance of the ring-shaped member.
Figure 10B:
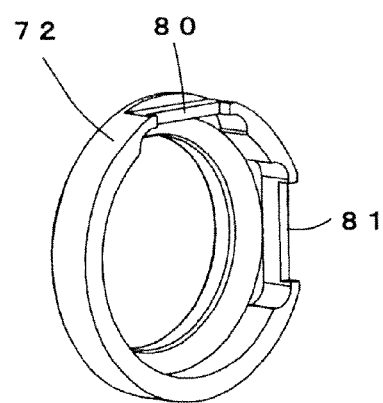
Figure 11A:
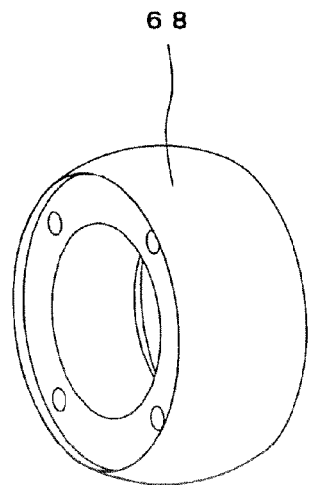
FIG. 11A and FIG. 11B illustrate explanatory drawings of the appearance of the spherical member.
Figure 11B:
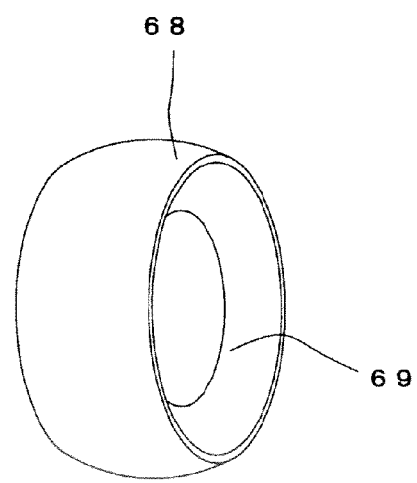

FIG. 3 illustrates the top view of the head and the alignment mechanism, FIG. 4 illustrates its front view, and FIG. 5 illustrates its side view. Although FIG. 6 to FIG. 8 illustrate the internal constitutions when the head is vertically rotated, the explanation on the electrical wiring is herein omitted.

A sample-supporting part 51 which supports the sample is provided on the surface side of the head 32. The sample-supporting part 51 has a fixedly-contacting part 52 which contacts the prescribed lateral side of the sample, and a movably-contacting part 53 which is provided at a position opposed to the fixedly-contacting part 52 and moves toward the fixedly-contacting part 52 to sandwich the sample.

The movably-contacting part 53 is connected with a lever 54, the sample is sandwiched between the movably-contacting part 53 and the fixedly-contacting part 52 by moving the lever 54, and the sandwiching of the sample can be released by moving the lever 54 in a direction for release.

An alignment mechanism 50 on the back side of the head 32 is constituted so as to be connected with the head 32, and the alignment mechanism 50 includes a vertical adjusting knob 60 which adjusts the alignment of the head 32 in a vertical direction and a horizontal adjusting knob 62 which adjusts the alignment of the head in a horizontal direction perpendicular to the vertical direction.

A fixation lever 64 which, after adjusting the alignment of the head 32 in the vertical or horizontal direction, fixes the head 32 at this orientated position is provided on the alignment mechanism 50.

As shown in FIG. 6 to FIG. 8, the Peltier element 36 for cooling the supported sample is provided on the back side of the sample-supporting part 51 in the head 32. The heatsink 38 for absorbing heat of the Peltier element 36 by the refrigerant is attached to the back side of the Peltier element 36. Two pipings, refrigerant piping 40a on a side allowing the refrigerant to inflow into the heatsink 38 and refrigerant piping 40b which allows the refrigerant discharged from the heatsink 38 to flow, are connected to the heatsink 38.

A chassis 66 of the head 32 is connected with a ball bearing provided in the alignment mechanism 50 so that it is vertically and horizontally rotatable. The ball bearing has a spherical member 68 having a spherical outer periphery, a holding member 70 in contact with the outer periphery of the spherical member 68 and slidably holding the spherical member 68, and a fixing holding member 71, and the chassis 66 of the head 32 is connected with the spherical member 68. The head 32 can be fixed at a prescribed orientated position by fastening the fixing holding member 71 with the fixation lever 64. In addition, the holding member 70 and the fixing holding member 71 represent the retainer portion in Claims.

Furthermore, an inner periphery 69 on the back side of the spherical member 68 is spherically shaped, and a ring-shaped member 72 having a spherical outer periphery is provided in contact with the back side of the spherical member 68 in order to slide the spherical member 68 relative to the holding member 70 and the fixing holding member 71.

A through hole 74 communicating between the inside of the head 32 and the hollow portion 43 of the coupling portion 41 is formed in the center of the spherical member 68. The refrigerant piping 40 connected with the heatsink 38 is provided through the through hole 74.

Also, a second through hole 75 communicating with the through hole 74 is formed in the center of the ring-shaped member 72. The refrigerant piping 40 is provided through the through hole 74 and the second through hole 75.

In addition, the refrigerant piping 40 is constituted of a concertina member 76 so that its part in the spherical member 68 and the ring-shaped member 72 can freely rotate in any angle. Thereby, in any angle that the spherical member 68 turns in the alignment mechanism 50, the part can follow the angle, and therefore breakage or the like of the refrigerant piping 40 can be prevented at this part.

As mentioned above, the head 32 and the alignment mechanism 50 are integrally constituted, and a coupling portion 78 for connecting the coupling portion 41 is provided on the back side of the alignment mechanism 50. In this embodiment, the coupling portion 41 is constituted as a cylindrical member (dashed line), and the coupling portion 78 connects the end part of the cylindrical coupling portion 41. A heat insulator is given around the coupling portion 41, and the hollow portion 43 in the coupling portion 41 is also filled with the heat insulator, and thereby increased temperature of the refrigerant can be prevented.

A seal member 79 which seals the space between the coupling portion 41 and a hollow portion 43 is given to the coupling portion 78, and in the center of the seal member 79, the end part of the refrigerant piping 40 passing through the ring-shaped member 72 is provided with the end part projecting. The end part of the refrigerant piping 40 is formed in a shape allowing connection with an end part of a tubular refrigerant piping 40c located in the coupling portion 41.

FIG. 9 to FIG. 11A and FIG. 11B illustrate the appearances of the spherical member, the ring-shaped member and the vertical moving member in the alignment mechanism.

A first linear portion 80 which is horizontally and linearly formed and a second linear portion 81 which is vertically and linearly formed are formed on the periphery of the ring-shaped member 72 in contact with the inner periphery on the back side of the spherical member 68.

In this embodiment, the first linear portion 80 is formed on the upper part of the periphery of the ring-shaped member 72, and the second linear portion 81 is formed on the right side (surface from a back view) of the periphery of the ring-shaped member 72.

A vertical moving member 82 which can push or lift the first linear portion 80 is connected with the first linear portion 80 while its axis direction is vertical, in order to vertically move the ring-shaped member 72. The vertical moving member 82 is threadably connected with the vertical adjusting knob 60 and vertically moves by turning the vertical adjusting knob 60.

On the end part of the vertical moving member 82, a gap 83 is formed so that the first linear portion 80 is sandwiched between the upper and lower parts. When the vertical moving member 82 vertically moves, the upper and lower surfaces of the gap 83 push the upper or under surface of the first linear portion 80, and thereby the ring-shaped member 72 vertically moves.

In order to move the ring-shaped member 72 in a horizontal direction perpendicular to the vertical direction, a horizontal moving member 84 which can push or lift the second linear portion 81 is connected with the second linear portion 81 while its axis direction is horizontal (right and left). The horizontal moving member 84 is threadably connected to a horizontal adjusting knob 61, and the vertical moving member 82 horizontally moves by turning the horizontal adjusting knob 61.

The constitution of the horizontal moving member 84 is the same as that of the vertical moving member 82, and the gap 83 is formed on its end part so that the second linear portion 81 is sandwiched between the right and left parts. When the horizontal moving member 84 horizontally moves, the right and left surfaces of the gap 83 push the right or left face of the second linear portion 81, and thereby the ring-shaped member 72 horizontally moves.

When the vertical moving member 82 is moved, it can freely move vertically while the horizontal moving member 84 is not impeditive even when the ring-shaped member 72 vertically moves, because the gap 83 on the end part of the horizontal moving member 84 is simply located at a position where it horizontally sandwiches the second linear portion 81.

When the horizontal moving member 84 is moved, it can freely move horizontally while the vertical moving member 82 is not impeditive even when the ring-shaped member 72 horizontally moves, because the gap 83 on the end part of the vertical moving member 82 is simply located at a position where it vertically sandwiches the first linear portion 80.

In relation to the vertical moving member 82 and the horizontal moving member 84, a plane part 89 having a flat surface parallel to the axis direction of each of the members 82 and 84 is formed on the end part having the gap 83.

The plane part 89 is constantly in contact with a plane wall 93 formed facing to the surface side of the holding member 70 and prevents the vertical moving member 82 and the horizontal moving member 84 from rotating themselves even when the vertical adjusting knob 60 and the horizontal adjusting knob 61 are rotated, and the vertical moving member 82 and the horizontal moving member 84 move only in the axis direction.

Thus the ring-shaped member 72 is vertically and horizontally moved, and thereby the spherical member 68 in contact with the outer periphery of the ring-shaped member 72 vertically and horizontally rotates along the spherical surfaces of the inner walls of the holding member 70 and the fixing holding member 71.

Thereby the angle of the sample can be adjusted relative to the cutting blade 20 of the head 32 with a high degree of accuracy.

Figures 12A, 12B:
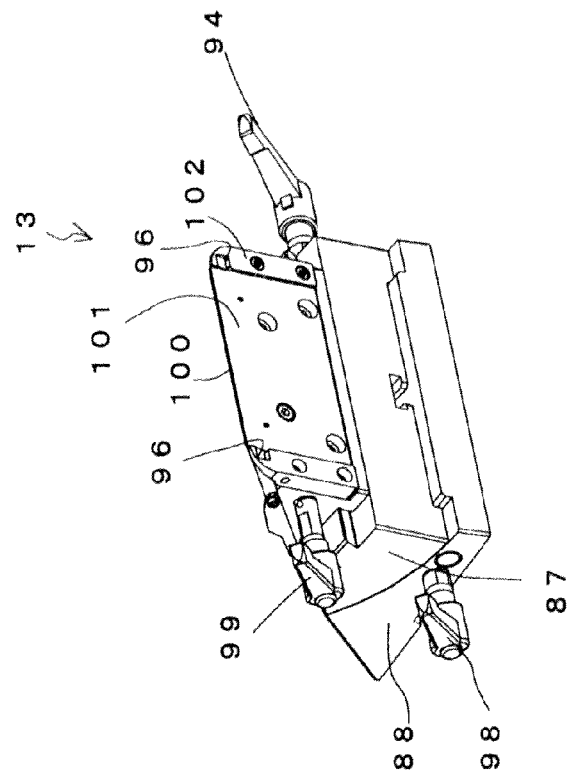
FIG. 12A and FIG. 12B illustrate explanatory drawings of the appearance of the blade holder.

Subsequently the constitution of the blade holder will be explained on the basis of FIG. 12A and FIG. 12B.

The blade holder 13 is constituted so that the attachment part 90 for attaching the cutting blade 20 is provided on a trapezoidal seating 88 and a blade angle-adjusting seating 87. A rail part 91 projecting upward and extending horizontally is formed on the top surface of the blade angle-adjusting seating 87, and a concave part 92 fitted to the rail part 91 is formed on the under surface of the attachment part 90. Thereby the attachment part 90 can horizontally slide on the blade angle-adjusting seating 87 along the rail part 91.

The attachment part 90 can horizontally slide by turning a fixation lever 94 in a direction for release, and it is fixed on this position by turning the fixation lever 94 in a direction for fixation.

The cutting blade 20 of which the longitudinal direction is horizontal and the blade is formed on an end surface of the longitudinal direction is attached to a superior end of the attachment part 90.

A blade fixture 100 having a slope to which the section prepared by slicing the sample is located is provided ahead of (in front of) the attached position of the cutting blade 20. The cutting blade 20 is attached to a space 104 (the attachment space in Claims) between the blade fixture 100 and the blade rest 101 which is positioned on a superior end of the attachment part 90 and on the back side of the blade fixture 100.

The blade fixture 100 can approach and leave from the blade rest 101 and can fix and release the cutting blade 20 by broadening and narrowing a gap of the space 104 allowing the cutting blade 20 to enter. Approach and leaving between the blade fixture 100 and the blade rest 101 can be conducted by turn of a fixation lever 99.

The cutting blade 20 is attached so that it enters the space 104 from any one of right or left while the space 104 between the blade fixture 100 and the blade rest 101 is broaden. After the cutting blade 20 is advanced to a prescribed position, the gap of the space 104 is narrowed by moving the fixation lever 99, and the cutting blade 20 is inserted between the blade fixture 100 and the blade rest 101 for fixation.

In addition, cutting blade guides 102 are attached to the right and left lateral sides of the blade rest 101. Magnets 96 and 96 are respectively provided on both of the right and left end parts of the cutting blade guides 102 to attract the both end parts of the longitudinal direction of the cutting blade 20 by magnetic force.

Particularly when the cutting blade 20 is replaced, there is no need to worry about falling of the cutting blade 20 from the space 104 to the chamber 11, and therefore it can be stably replaced and its detachment can be also facilitated by providing the two magnets 96 in this way.

Additionally, the lever 98 provided on the lateral side of the trapezoidal seating 88 is for fixation of the trapezoidal seating 88 into the chamber 11 and release of the fixation.

What is claimed is:

1. A microtome comprising:
a cutting blade attached to a blade holder;
a head which holds a sample so that a front face side of the sample faces the cutting blade;
an alignment mechanism which is provided on a back face side of the head and aligns said head so that the head is rotatable in a vertical direction and is rotatable in a horizontal direction perpendicular to the vertical direction;
a body portion which is provided on a back face side of the alignment mechanism and has a contact separation mechanism allowing the head to contact with and separate from the cutting blade;
a cylindrical coupling portion which has a hollow portion formed in its center and couples the body portion with the head;
a temperature controller provided in the head for cooling or heating the sample held by the head; and
refrigerant piping for circulating a refrigerant in the temperature controller, and electrical wiring for the temperature controller, wherein:
said alignment mechanism includes a spherical member coupled with the back face side of the head and having a spherical outer periphery, and a retainer portion for slidably retaining the outer periphery of the spherical member along the spherical surface;
in said spherical member, a through hole communicating with the hollow portion of said coupling portion is formed; and
said refrigerant piping and electrical wiring are connected with the temperature controller in the head through the through hole of the spherical member and the hollow portion of the coupling portion.

2. The microtome according to claim 1, wherein:
an inner wall surface on a rear face side of said spherical member is spherically formed;
a ring-shaped member is provided in which its outer periphery is spherically formed so as to be slidable in contact with the inner wall surface of the spherical member and a second through hole communicating with said through hole and said hollow portion is formed in the center;
vertically moving means is provided which vertically rotates the head by vertically moving the ring-shaped member; and
horizontally moving means is provided which horizontally rotates the head by horizontally moving the ring-shaped member.

3. The microtome according to claim 2, wherein:
said vertically moving means has a first linear portion which is horizontally and linearly formed on an upper edge or lower edge of the ring-shaped member and a vertically pressing shaft which is freely movable horizontally relative to the first linear portion and is formed to be capable of vertically pressing the first linear portion; and
said horizontally moving means has a second linear portion which is vertically and linearly formed on a left side or right side of the ring-shaped member, and a horizontally pressing shaft which is freely movable vertically relative to the second linear portion and is formed to be capable of horizontally pressing the second linear portion.

4. The microtome according to claim 1, wherein said refrigerant piping located in the through hole includes a member which is bendable in any direction.

5. The microtome according to claim 1, wherein:
said coupling portion has an introduction hole formed for introducing the refrigerant piping and the electrical wiring into the hollow portion of the coupling portion; and
the refrigerant piping and the electrical wiring positioned from the introduction hole to the outside of the coupling portion are arranged in a curved manner so as to be capable of following the movement of the coupling portion by said contact separation mechanism.

6. The microtome according to claim 1, wherein said blade holder has an attachment space formed for the cutting blade to enter therein for attachment and is equipped with magnets for attracting the cutting blade that has entered the attachment space.

7. A cryostat comprising a chamber having a cooling function and the microtome according to claim 1.

8. The cryostat according to claim 7, wherein only the blade holder to which the cutting blade is attached and the head of the microtome are arranged in said chamber.

9. The cryostat according to claim 8, wherein a portion from which the head of the microtome projects is covered with a deformable and fluid-tight member in an inner wall surface of said chamber.

10. A cryostat comprising a chamber having a cooling function and the microtome according to claim 2.

11. A cryostat comprising a chamber having a cooling function and the microtome according to claim 3.

12. A cryostat comprising a chamber having a cooling function and the microtome according to claim 4.

13. A cryostat comprising a chamber having a cooling function and the microtome according to claim 5.

14. A cryostat comprising a chamber having a cooling function and the microtome according to claim 6.

* * * * *